(12) United States Patent
Becker et al.

(10) Patent No.: US 7,344,749 B2
(45) Date of Patent: Mar. 18, 2008

(54) METHOD FOR COATING A SUBSTRATE WITH CALCIUM PHOSPHATE

(75) Inventors: Petra Becker, Rostock (DE); Mischa Buhrmeister, Rostock (DE); Hans-Georg Neumann, Rostock (DE); Marianne Teller, Mistorf (DE)

(73) Assignee: DOT GmbH, Rostock (DE)

( * ) Notice: Subject to any disclaimer, the term of this patent is extended or adjusted under 35 U.S.C. 154(b) by 410 days.

(21) Appl. No.: 10/498,732

(22) PCT Filed: Dec. 6, 2002

(86) PCT No.: PCT/EP02/13819

§ 371 (c)(1),
(2), (4) Date: Jun. 15, 2004

(87) PCT Pub. No.: WO03/052164

PCT Pub. Date: Jun. 26, 2003

(65) Prior Publication Data

US 2005/0069629 A1    Mar. 31, 2005

(30) Foreign Application Priority Data

Dec. 15, 2001 (DE) ................. 101 61 827

(51) Int. Cl.
A61L 33/00 (2006.01)
A61K 6/083 (2006.01)
B05D 3/00 (2006.01)
B05D 3/12 (2006.01)

(52) U.S. Cl. ............ 427/2.1; 427/2.24; 427/2.26; 427/2.27; 427/294; 427/350

(58) Field of Classification Search ............... None
See application file for complete search history.

(56) References Cited

U.S. PATENT DOCUMENTS 5,849,569 A * 12/1998 Davies ............... 435/288.3
6,153,266 A    11/2000 Yokogawa et al.
6,323,146 B1 * 11/2001 Pugh et al. .............. 501/1

FOREIGN PATENT DOCUMENTS

| EP | 0322250 | 6/1989 |
| EP | 0322250 A1 * | 6/1989 |
| EP | 0347028 | 12/1989 |
| EP | 0347028 A2 * | 12/1989 |

OTHER PUBLICATIONS

"Drying" from Wikipedia, http://en.wikipedia.org/wiki/Drying accessed May 24, 2007.*
"Vacuum Drying" from The American Heritage Dictionary, Second College Edition, Boston: Houghton-Mifflin Company, 1985 pp. 1334.*

* cited by examiner

Primary Examiner—Timothy Meeks
Assistant Examiner—Kelly M Stouffer
(74) Attorney, Agent, or Firm—Jordan and Hamburg LLP

(57) ABSTRACT

A method for coating substrates with calcium phosphate. The aim of the method is to be able to carry out a simple coating for all materials as well as for particles. To this end, the substrate to be coated is placed in a calcium phosphate gel, whereupon this substrate that is coated with the gel is dried. Afterwards, the calcium phosphate particles not adhering to the substrate are removed. The substrate can also be placed inside a colloidal solution of $SiO_2$ containing a calcium phosphate, whereupon the mixture is constantly set in motion, the solvent is removed, and the substrate is provided with a calcium phosphate layer by condensing the colloidal $SiO_2$ on the surface of the substrate. The coated substrates can, particularly when it concerns coated particles, be used as a bone substitute material.

10 Claims, No Drawings

METHOD FOR COATING A SUBSTRATE WITH CALCIUM PHOSPHATE

BACKGROUND OF THE INVENTION

The invention relates to a method for coating a substrate with a calcium phosphate layer.

The plasma spray method is used to coat substrates in particular with a bioactive calcium phosphate layer, e.g. hydroxyapatite. However, this method is unsuitable if the substrate consists of small particles or is not resistant to heat. Electrochemical deposition of calcium phosphate is likewise inapplicable to particles even if the particles are electrically conducting.

U.S. Pat. No. 6,153,266 describes a method for producing a calcium phosphate layer, in which in a first step the substrate is immersed in a phosphate-containing bath which contains no calcium. The substrate is subsequently removed from the solution, dried and immersed in a second solution which has a ph of 8 and contains calcium. Calcium phosphate is formed on the surface of the substrate in this solution. The first disadvantage of this method is that the coating is carried out with 2 method steps. A further disadvantage is that it is not possible with the 2-step method to produce the layer thickness in the desired scope. For thick layers, therefore, the known method provides a further method step in which the substrate provided with the calcium phosphate layer is immersed in a calcium phosphate solution.

SUMMARY OF THE INVENTION

The object on which the invention is based is to eliminate the disadvantages of the known methods and to produce in a simple method a calcium phosphate layer which has a desired layer thickness.

This object is achieved according to the invention, the substrate being introduced into a calcium phosphate gel, and the substrate coated with the gel being dried and separated from calcium phosphate particles. "Gel" means a liquid in a paste-like state.

According to the invention it is also possible to apply the calcium phosphate layer directly to the surface of the substrate by introducing the substrate into a calcium phosphate-containing silicon dioxide colloid and subsequently generating a crack-free coating film by removing the solvent.

Advantageous refinements of the invention are described in the disclosure.

The advantage of the method of the invention is that it is possible to provide a substrate with a calcium phosphate layer in one step. Since the layer thickness depends on the concentration of the calcium phosphate gel or of the colloid solution, a desired layer thickness can be produced by adjusting the concentration. The method is suitable for coating large-area substrates and particles. It does not depend on the material of which the substrate consists.

The strength of adhesion of the layer to the substrate can be increased by removing the gas (air) present on the substrate by applying a reduced pressure. This method is particularly advantageous if the substrate has pores. The air is then removed from the pores, and the calcium phosphate gel can penetrate into the pores. It is regarded as a further advantage that it is possible through a suitable composition of the gel to produce the layer from various calcium phosphate modifications. This is particularly important for a bioactive layer. It is known that the degree of bioactivity of a layer increases with its instability in a physiological environment. Calcium phosphates whose solubility is very much higher than that of hydroxyapatite, such as bruschite and monetite, are particularly important specifically for the phase of incorporation into the bone. If the coated particles are to be used with the aim of improving the union of the substrate with bone tissue, the gel consists of bruschite and/or monetite or a mixture of bruschite and/or monetite and hydroxyapatite. The gel may, however, also consist of a mixture of silica gel and calcium phosphate. It may additionally comprise fillers such as calcium sulfate or factors having an osteoinductive effect. It is also possible to introduce into the layer medicaments such as antibiotics or agents which speed growth of bone or inhibit degradation of bone, for example by mixing them into the gel.

The substrates coated using the method of the invention are particularly suitable as bone substitute for filling bone defects or for filling in a gap between an implant and a bone into which the implant has been inserted. Coated substrate particles which are biocompatible are preferably used for these purposes. The particles may also serve to anchor the implant in the bone.

DETAILED DESCRIPTION OF THE INVENTION

The invention is explained in more detail below by means of examples without being restricted thereto.

EXAMPLE 1

A phosphate acid solution is introduced with continuous stirring into a calcium hydroxide solution. The fine precipitate which forms is concentrated by centrifugation and separated from the supernatant clear solution. Titanium granules which have previously been degreased and cleaned are introduced into the calcium phosphate gel obtained in this way and are thoroughly mixed. This mixture is put in a reduced pressure chamber. When a suitable reduced pressure is applied, the air is removed from the pores of the titanium granules. On subsequent ventilation, the calcium phosphate gel penetrates into the pores. The coated granules are dried, isolated and separated from fallen calcium phosphate particles by screening. The calcium phosphate layer thickness is variable and can be adjusted via the concentration of the prepared gel.

EXAMPLE 2

Any suitable calcium phosphate powder is mixed with a silica gel. Degreased and cleaned titanium granules are introduced into this gel and thoroughly mixed. As in example 1, the air is removed from the pores of the titanium granules in order to make it possible for the calcium phosphate silica gel to penetrate into the pores on ventilation. The coated granules are dried, isolated and separated from precipitated calcium phosphate-silica particles by means of a stream of air. The layer thickness of the calcium phosphate silicate can be adjusted via the concentration of the gel.

EXAMPLE 3

Any suitable calcium phosphate powder is introduced into a hydrophilic colloid of the product of the hydrolysis of an alkoxysilane (e.g. TEOS) and uniformly distributed by stirring. Subsequently, while stirring further, titanium powder or granules of any particle size are introduced into this colloidal solution and, after thorough mixing, cautious removal of the solvent by distillation is started while agitating continuously. The completion of coating is characterized by the titanium particle becoming pourable and a crack-free film forming directly on the substrate surface. The coated substrate is finally heat-treated in several stages up to 150° C.

The invention claimed is:

1. A method for providing a dried calcium phosphate layer coating on a porous substrate, comprising:
   introducing the porous substrate into a calcium phosphate gel,
   then removing air contained on said porous substrate by applying a reduced pressure,
   then ventilating said porous substrate and said gel, and
   then drying the porous substrate and the gel,
   whereby the porous substrate is provided with said dried calcium phosphate layer coating.

2. A method for providing a dried calcium phosphate layer coating on a porous substrate, comprising:
   introducing the porous substrate into a calcium phosphate-containing colloidal $SiO_2$ solution or a calcium phosphate-containing $SiO_2$ gel,
   then removing air contained on said porous substrate by applying a reduced pressure,
   then ventilating said porous substrate and said colloidal $SiO_2$ solution or said porous substrate and said $SiO_2$ gel, and
   then drying said porous substrate and said colloidal $SiO_2$ solution or said $SiO_2$ gel,
   whereby the porous substrate is provided with said dried calcium phosphate layer coating.

3. The method as claimed in claim 1 or 2, further comprising predetermining a thickness of the layer by setting a concentration of the calcium phosphate gel or the colloidal $SiO_2$ solution or the $SiO_2$ gel, respectively.

4. The method as claimed in claim 1, wherein the calcium phosphate gel comprises bruschite and/or monetite or a mixture of bruschite and/or monetite and hydroxyapatite.

5. The method as claimed in claim 1, wherein the gel comprises a mixture of silica gel and calcium phosphate.

6. The method as claimed in claim 2, wherein the colloidal solution comprises hydroxyapatite and/or β-tricalcium phosphate.

7. The method as claimed in claim 1 or 2, wherein the calcium phosphate gel or the colloidal $SiO_2$ solution or the $SiO_2$ gel, respectively, comprises osteoinductive factors.

8. The method as claimed in claim 1 or 2, wherein the calcium phosphate gel or the colloidal $SiO_2$ solution or the $SiO_2$ gel, respectively, comprises medicaments.

9. The method according to claim 1, further comprising separating the porous substrate provided with said dried calcium phosphate layer coating from residual calcium phosphate particles which do not form part of said dried calcium phosphate layer coating.

10. The method according to claim 2, further comprising separating the porous substrate provided with said dried calcium phosphate layer coating from residual calcium phosphate particles which do not form part of said dried calcium phosphate layer coating.

* * * * *